(12) United States Patent
Seong et al.

(10) Patent No.: US 9,629,854 B2
(45) Date of Patent: Apr. 25, 2017

(54) COMPOSITION COMPRISING GPCR19 AGONIST AS AN ACTIVE INGREDIENT FOR PREVENTING OR TREATING ALLERGIC DERMATITIS

(71) Applicant: Seoul Techno Holdings, Inc., Seoul (KR)

(72) Inventors: Seung Yong Seong, Seoul (KR); Youn Hee Kim, Seoul (KR)

(73) Assignee: SEOUL TECHNO HOLDINGS, INC, Seoul (KR)

( * ) Notice: Subject to any disclaimer, the term of this patent is extended or adjusted under 35 U.S.C. 154(b) by 0 days.

(21) Appl. No.: 14/440,875

(22) PCT Filed: Mar. 5, 2014

(86) PCT No.: PCT/KR2014/001819
§ 371 (c)(1),
(2) Date: May 5, 2015

(87) PCT Pub. No.: WO2015/030328
PCT Pub. Date: Mar. 5, 2015

(65) Prior Publication Data
US 2015/0290219 A1    Oct. 15, 2015

(30) Foreign Application Priority Data

Aug. 26, 2013  (KR) .................... 10-2013-0100813

(51) Int. Cl.
| | | |
|---|---|---|
| *A61K 8/02* | (2006.01) | |
| *A61K 8/72* | (2006.01) | |
| *A61K 38/00* | (2006.01) | |
| *A61K 31/575* | (2006.01) | |
| *A61K 9/00* | (2006.01) | |
| *A61K 47/32* | (2006.01) | |
| *A61K 9/20* | (2006.01) | |
| *A61K 8/31* | (2006.01) | |
| *A61Q 5/06* | (2006.01) | |
| *A61K 8/81* | (2006.01) | |
| *A61K 8/85* | (2006.01) | |
| *A61K 8/88* | (2006.01) | |
| *A61K 8/891* | (2006.01) | |
| *A61K 8/92* | (2006.01) | |

(52) U.S. Cl.
CPC .......... *A61K 31/575* (2013.01); *A61K 8/0216* (2013.01); *A61K 8/31* (2013.01); *A61K 8/8117* (2013.01); *A61K 8/8164* (2013.01); *A61K 8/85* (2013.01); *A61K 8/88* (2013.01); *A61K 8/891* (2013.01); *A61K 8/922* (2013.01); *A61K 9/0014* (2013.01); *A61K 9/0019* (2013.01); *A61K 9/2059* (2013.01); *A61K 47/32* (2013.01); *A61Q 5/06* (2013.01); *A61K 2800/805* (2013.01)

(58) Field of Classification Search
None
See application file for complete search history.

(56) References Cited

U.S. PATENT DOCUMENTS

| 6,043,046 A | 3/2000 | Ito et al. |
|---|---|---|
| 2008/0214451 A1 | 9/2008 | Kuliopulos et al. |

FOREIGN PATENT DOCUMENTS

| JP | 2011-079856 A | 4/2011 |
|---|---|---|
| KR | 10-0785656 B1 | 12/2007 |
| KR | 10-2013-0054702 A | 5/2013 |

OTHER PUBLICATIONS

The K-Zone: Biophysical data tables: standard man; published 1994-2006; downloaded Mar. 14, 2009.*
Silva et al.; Brazilian Journal of Pharmaceutical Sciences; vol. 48, n. 4, Oct./Dec. 2012.*

* cited by examiner

*Primary Examiner* — Jeffrey T Palenik
(74) *Attorney, Agent, or Firm* — Novick, Kim & Lee, PLLC; Jae Youn Kim

(57) ABSTRACT

The present invention is about a pharmaceutical composition, an oral preparation, and an injection preparation containing a G protein-coupled Receptor19 (GPCR19) agonist, specifically sodium taurodeoxycholate (HY2191) and its derivative, as an active ingredient for preventing or treating allergic skin diseases. The present invention is also about an external preparation and a cosmetic composition containing said pharmaceutical composition for preventing and improving allergic skin diseases. The said pharmaceutical composition shows an excellent efficacy in treating and improving allergic dermatitis compared with the steroid ointments or immunosuppressive ointments currently used. The said pharmaceutical composition reduces the level of serum IgE, which is a major factor causing allergic dermatitis, increases TH1 cytokine alleviating allergic dermatitis and reduces TH2 cytokine that exacerbates allergic dermatitis. The said pharmaceutical composition also reduces infiltration of a mast cell, eosinophil, and neutrophil in dermis and ameliorates clinical symptoms such as erythema, hemorrhage, edema, excoriation, erosion, scaling and dryness. Thus, the said pharmaceutical composition can be used to prevent and treat allergic skin diseases.

8 Claims, 7 Drawing Sheets

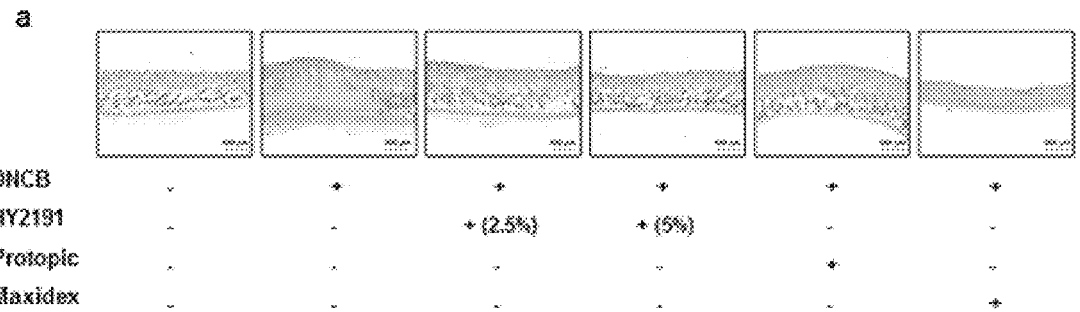
FIG. 5a
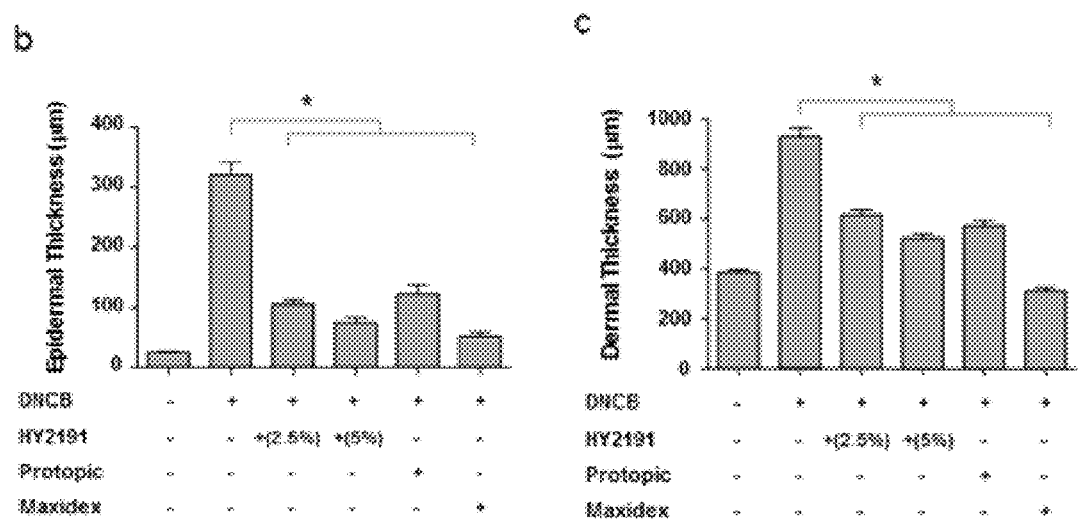
FIG. 5b
FIG. 5c

COMPOSITION COMPRISING GPCR19 AGONIST AS AN ACTIVE INGREDIENT FOR PREVENTING OR TREATING ALLERGIC DERMATITIS

TECHNICAL FIELD

The present invention is about a pharmaceutical composition containing a G protein-coupled Receptor19 (GPCR19) agonist, specifically sodium taurodeoxycholate (HY2191) and its derivative, as an active ingredient, for preventing or treating allergic skin diseases. The present invention is about an oral preparation and an injection preparation containing the GPCR19 agonist, specifically sodium taurodeoxycholate (HY2191) and its derivative, as an active ingredient, for preventing or treating allergic skin diseases. The present invention is also about an external preparation and a cosmetic composition containing the GPCR19 agonist, specifically sodium taurodeoxycholate (HY2191) and its derivative, as an active ingredient for preventing and improving allergic skin diseases.

BACKGROUND ART

A predisposition developing dermatitis, asthma, or hay fever in response to specific foods and respiratory exposure to specific substance was first described as "atopy" by Coca in 1925. Atopic diseases include asthma, allergic rhinitis, allergic conjunctivitis and atopic dermatitis, etc. The incidence of atopic dermatitis has rapidly increased in worldwide due to increased environmental pollutants. The prevalence of atopic disease reaches 20% of normal individuals in worldwide. The quality of lives of patients having atopic dermatitis is very poor since their daily lives are constrained and affected by the symptoms. The financial burden of the society for the prevention and treatment of atopic dermatitis has also increased drastically. Accordingly, the development of effective medicines to manage or treat atopic diseases is urgently required.

Atopic dermatitis is a chronic and recurrent skin disease with severe pruritus, mostly starting in infancy or in early childhood. It is one of the most common skin diseases associated with a family history. Symptoms begin in infancy or childhood, particularly at about 2 months old. Approximately 50% of total atopic dermatitis cases affect children under 2 years old and the most cases affect children under 5 years old. It is very rare for atopic dermatitis to develop in adult stage without a childhood history. In some cases, symptoms may alleviate or disappear as patients grow up. More than 50% of children with atopic dermatitis show improved symptoms after 2 years old.

Atopic dermatitis is characterized by morphology and distribution of skin lesion and is accompanied by pruritus (itchiness), xeroderma and characteristic eczema. Atopic dermatitis starts with eczema in the face, arms and legs in early childhood, but as children grow, atopic dermatitis is observed as eczema in front of the elbows and behind the knees. Lichenification (thickening of skin fold) progress in adult patients and eczema often occurs in the face, chest, neck in addition to legs and arms, which is comparable with infants and young children.

Atopic skin disease usually accompanies other allergic reaction(s). Atopic dermatitis is not only a skin disease but also a signal of allergic march, such as allergic asthma or rhinitis. The initiation and pathogenesis of atopic dermatitis, however, has not yet been well defined. For this reason, a medication that can completely cure atopic dermatitis has not yet been developed.

At present, anti-histamines, steroids or immunomodulators have been used for treating atopic dermatitis. However, when the medication dosage is reduced or administration is stopped, symptoms usually recur. Furthermore, a long-term administration may incur systemic side effects such as hypoadrenocorticism, diabetes, peptic ulcer, hirsutism, alopecia, pigmentation and cataract (especially in infants). The steroid ointments frequently incur serious side effects such as skin atrophy, facial flushing caused by prominent capillaries and folliculitis, etc. Elidel (pimecrolimus) cream and Protopic (tacrolimus, FK506) ointment were developed to replace steroid ointments. Since these medications show no side effects shown by steroid ointments even though they are applied for a long time, the market of these drugs has grown rapidly, accounting 30% of the atopic dermatitis market. However, it was suggested that calcineurin inhibitor might cause cancer. For this reason, only a low dosage of calcineurin inhibitor is allowed for patients under 16 years old. Administration of calcineurin inhibitor is not allowed for an infant under 2 years old. Because of the carcinogenesis of the drugs, market size has drastically decreased.

Anti-histamines may be used to control pruritus. An ultraviolet treatment and an interferon treatment also have been used in some cases. However, in most cases, symptoms are relieved only for a short time and recurred when the administration is stopped. Thus, the atopy is considered as an incurable disease currently. This is why there is an urgent need to develop new drugs to treat and prevent atopy with better efficacy and less side effects than current medicines.

The inventors of the present invention have found that a composition containing a GPCR19 agonist, specifically sodium taurodeoxycholate (HY2191) and its derivatives, is considerably effective in treating atopic dermatitis. The present invention suggests the pharmaceutical compound containing the GPCR19 agonist is useful for preventing, treating and improving atopic dermatitis. Until now, not a single example has been provided for the application of the composition containing sodium taurodeoxycholate (HY2191) and its derivatives in improving, preventing and treating atopic dermatitis. Furthermore, its effectiveness on atopy has neither been reported.

SUMMARY OF INVENTION

Technical Problem

The objective of the present invention is to provide a composition containing a GPCR19 agonist as an active ingredient for preventing or treating allergic skin diseases, and more specifically, to provide a composition containing sodium taurodeoxycholate (HY2191) as one of GPCR19 agonists and its derivative as active ingredients for preventing or treating allergic skin diseases. Still more specifically, an objective of the present invention is to provide a medication containing sodium taurodeoxycholate (HY2191) and its derivative as active ingredients for preventing, treating, or improving allergic skin diseases.

Solution to Problem

In order to achieve the objectives described above, the present invention provides a pharmaceutical composition containing a GPCR19 agonist as an active ingredient, or more specifically, a pharmaceutical composition containing sodium taurodeoxycholate (HY2191) and its derivatives as active ingredients for preventing or treating allergic skin diseases. The pharmaceutical composition can be manufactured in the form of an external preparation, an injection preparation, and an oral preparation, and a pharmaceutically acceptable additive may be added thereto.

Advantageous Effects of Invention

According to the present invention, the composition containing a GPCR19 agonist, specifically sodium taurodeoxycholate (HY2191) and its derivatives, shows an excellent efficacy in treating and improving allergic dermatitis better than steroid ointments or immunosuppressive ointments which are currently used in the market. Moreover, according to the present invention, the composition containing a GPCR19 agonist, specifically sodium taurodeoxycholate (HY2191) and its derivatives, do not show deleterious side effects that are frequently observed in patients who are treated with former medicines for atopic diseases, such as steroids or FK506 derivatives. Further, the composition for preventing and treating allergic skin diseases presented by the present invention drastically reduces the amount of serum IgE, a major biomarker of allergic dermatitis. The composition presented by present invention inhibits the function of type 2 T lymphocytes and accelerates the function of type 1 T lymphocytes that are frequently observed imbalance in atopy patients. Thus, the said composition presented by the present invention can be used as a medicine for preventing and treating allergic skin diseases.

BRIEF DESCRIPTION OF DRAWINGS

FIGS. 5a to 5c show changes in thicknesses of epidermis (B) and dermis (C) after staining with H&E (A) of mouse dorsal skins.

DESCRIPTION OF MOST PREFERRED EMBODIMENTS

Figure 1A:
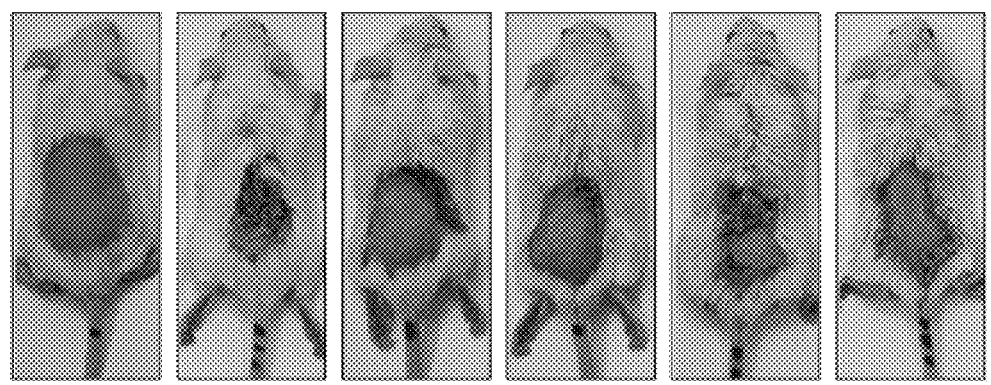
FIGS. 1a and 1b are photos of dorsal skin.

The present invention relates to a pharmaceutical composition containing a G protein-Coupled Receptor19 (GPCR19) agonist as an active ingredient for preventing or treating allergic skin diseases.

Further, the present invention relates to a cosmetic composition containing a G protein-Coupled Receptor19 (GPCR19) agonist as an active ingredient for preventing or improving allergic skin diseases.

[Description of Embodiments ]

The present invention is about a pharmaceutical composition containing a G protein-Coupled Receptor19 (GPCR19) agonist as an active ingredient for preventing or treating allergic skin diseases.

In an exemplary embodiment of the present invention, the G protein-Coupled Receptor19 (GPCR19) agonist may be sodium taurodeoxycholate (HY2191) and its derivatives.

In an exemplary embodiment of the present invention, the GPCR19 agonist reduces the amount of serum IgE.

In an exemplary embodiment of the present invention, the GPCR19 agonist reduces serum TH2 cytokines and increases serum TH1 cytokines.

In an exemplary embodiment of the present invention, the GPCR19 agonist reduces the number of eosinophils, neutrophils, and mast cells in dermis affected by allergic skin diseases.

In an exemplary embodiment of the present invention, the GPCR19 agonist ameliorates clinical symptoms such as erythema, hemorrhage, edema, excoriation, erosion, scaling and dryness of atopic skins.

In another exemplary embodiment of the present invention, the composition containing a G protein-Coupled Receptor19 (GPCR19) agonist as an active ingredient may be provided as an ointment preparation, an oral preparation, or an injection preparation for preventing or improving allergic dermatitis.

In an exemplary embodiment of the present invention, the allergic skin diseases may be chosen from the group consists of allergic dermatitis, atopic dermatitis, contact dermatitis, hives, and pruritus.

To be more specific, the pharmaceutical composition may have any one formulation chosen from the group consists of tablet, pill, powder, granules, capsule, suspension, internal formulation, ointment, syrups, sterilized aqueous solution, non-aqueous solvent, suspension, emulsion, lyophilized formulation, suppositories, and injection formulation.

In an exemplary embodiment of the present invention, the G protein-Coupled Receptor19 agonist is administered at a dosage of 0.001 mg to 100 g/day, 0.01 mg to 10 g/day, or 0.1 mg to 1 g/day to a warm-blooded animal weighing 75 kg for prevention or treatment of allergic skin diseases, and, thus, the allergic skin diseases can be prevented or treated.

The dose of the G protein-Coupled Receptor19 agonist used for the present invention may depend on various factors such as efficacy, duration of action of the active ingredient, mode of administration, sex, age, weight and individual conditions of other accompanying diseases of warm-blooded animals. A specific administration route and a dose may be decided by a responsible doctor/veterinarian, depending on individual properties of the subject to be administered, i.e., age, weight, severity of a disease, and physical conditions, etc.

The composition may be administered through a certain general route as long as it can reach a target tissue. The composition of the present invention may be administered orally, intraperitoneally, intravenously, intramuscularly, subcutaneously, intradermally, intranasally, intrapulmonarly, intrarectally, but may not be limited thereto. Further, the composition may be administered by a certain device capable of moving the active ingredient to a target cell.

In an exemplary embodiment of the present invention, a pharmaceutical preparation for oral administration may be formulated in various ways such as sugar-coated tablets, tablets, pills, powder, granules, capsules, or ampules. The formulations are prepared by the methods known in the art, for example, typical mixing, granulation, tableting, dissolution, or lyophilization. For example, the pharmaceutical preparation for oral administration can be prepared by mixing an active ingredient with a solid carrier, granulating the mixture, adding an appropriate additive if necessary, and formulating the mixture or the granules into tablets or sugar-coated tablets.

Suitable carriers are especially fillers, such as sugars, for example lactose, saccharose, mannitol, sorbitol, or cellulose preparations and/or calcium phosphates, for example tricalcium phosphate or calcium hydrogen phosphate, and also binders, such as starch pastes using, for example, corn, wheat, rice, potato starch, gelatin, tragacanth, or methylcellulose and/or polyvinylpyrrolidone, if desired disintegrators, such as the above-mentioned starches, also carboxymethyl starch, crosslinked polyvinylpyrrolidone, agar, alginic acid or a salt thereof, such as sodium alginate.

Additives are especially flow conditioners and lubricants, for example, silicic acid, talc, stearic acid or a salt thereof, such as magnesium or calcium stearate, and/or polyethylene glycol. Dragee cores are provided with suitable coatings that may resistant to gastric juices, there being used, inter alia, concentrated sugar solutions which may contain gum arabic, talc, polyvinylpyrrolidone, polyethylene glycol and/or enriched sugar solution containing titanium dioxide, lacquer solutions in suitable organic solvents or solvent mixtures, or, for the production of coatings that are resistant to gastric juices, solutions of suitable cellulose preparations, such as acetylcellulose phthalate or hydroxypropylmethylcellulose phthalate.

Other pharmaceutical preparations for oral administration are capsules including dry-filled capsules made of gelatin and soft sealed capsules made of gelatin and a plasticizer, such as glycerol or sorbitol. The dry-filled capsules may contain the active substance in the form of granules, for example in a mixture with fillers, such as lactose, binders, such as starches, and/or glidants, such as talc or magnesium stearate, and optionally stabilizers. In soft capsules, the active substance is preferably dissolved or suspended in suitable liquids, such as fatty oils, paraffin oil or liquid polyethyleneglycols, and stabilizers may be added thereto.

Preparations for parenteral administration may include sterilized aqueous solutions, non-aqueous solvents, suspensions, emulsions, lyophilized preparations, and suppositoriums. Parenteral preparations may be injections effective in various administration methods such as intravenous, intraarterial, intramuscular, intraperitoneal, intranasal, intradermal, and subcutaneous administration methods, preferably an intravenous administration method. Such fluids are preferably isotonic aqueous solutions or suspensions which can be prepared before use, for example from lyophilized preparations which contain the active ingredient alone or together with a pharmaceutically acceptable carrier. The pharmaceutical preparations may be sterilized and/or may contain additives, for example preservatives, stabilizers, wetting agents and/or emulsifiers, solubilizers, salts to regulate the osmotic pressure and/or buffers such as buffer solution.

To be specific, non-aqueous solvents and suspensions may contain propylene glycol, polyethylene glycol, vegetable oil such as olive oil, injectable ester such as ethylolate, etc. Suppositories may contain witepsol, macrogol, tween 61, cacao butter, laurin butter, glycerinated gelatin, etc.

In an exemplary embodiment of the present invention, the G protein-Coupled Receptor19 agonist according to the present invention may be administered as a combination/mixture with other medicines for preventing or treating allergic skin diseases. Therefore, the present invention also includes a method for treating patients with allergic skin diseases including a treatment with a combination of the G protein-Coupled Receptor19 agonist and other different medicines for preventing/treating allergic skin diseases. In yet another exemplary embodiment of the present invention, there may be provided an external preparation for preventing or improving allergic dermatitis containing a G protein-Coupled Receptor19 (GPCR19) agonist as an active ingredient.

In an exemplary embodiment of the present invention, a composition of the external preparation may be selected from the group consisting of cream, gel, ointment, emulsion, suspension, spray, and a transdermal patch, but is not limited thereto.

In an exemplary embodiment of the present invention, the external preparation may be applied with the amount of 0.001 mg to 100 g, specifically 0.01 mg to 10 g, more specifically 0.1 mg to 1 g per day and may be applied from one to several times per day, specifically from one to three times per day. The external preparation may be applied until symptoms of allergic dermatitis are relieved.

In still another exemplary embodiment of the present invention, there may be provided a cosmetic composition containing a G protein-Coupled Receptor19 (GPCR19) agonist as an active ingredient for preventing or improving allergic dermatitis.

In an exemplary embodiment of the present invention, the G protein-Coupled Receptor19 (GPCR19) agonist may be sodium taurodeoxycholate (HY2191) and its derivatives.

In an exemplary embodiment of the present invention, the cosmetic composition may be prepared in any one or more formulations chosen from the group consists of soap, cleansing foam, cleansing cream, cleansing water, a bath product, skin lotion, skin softener, skin toner, lotion, cream, essence, astringent, emulsion, gel, lipstick, spray, shampoo, conditioner, treatment, body cleanser, pack, massage cream, face powder, compact, foundation, two-way cake, and makeup base for allergic skin diseases, but is not limited thereto.

In an exemplary embodiment of the present invention, the cosmetic composition may be commercialized as a formulation type chosen from the group consists of soap, cleansing foam, cleansing cream, cleansing water, and a bath product for allergic skin diseases.

In an exemplary embodiment of the present invention, the allergic skin diseases may be chosen from the group consists of allergic dermatitis, atopic dermatitis, contact dermatitis, hives, and pruritus.

If the formulation of the present invention is paste, cream, or gel, it may contain, as carrier components, animal oil, vegetable oil, wax, paraffin, starch, tragacanth, cellulose derivatives, polyethylene glycol, silicone, bentonite, silica, talc, or zinc oxide.

If the formulation of the present invention is powder or spray, it may contain, as carrier components, lactose, talc, silica, aluminum hydroxide, calcium silicate, or polyamide powder. Particularly, if it is spray, it may additionally contain a propellant, such as chlorofluorohydrocarbon, propane/butane, or dimethyl ether.

If the formulation of the present invention is solution or emulsion, it may contain, as carrier components, a solvent, a solubilizing agent, or an emulsifying agent, for example, water, ethanol, isopropanol, ethyl carbonate, ethyl acetate, benzyl alcohol, benzyl benzoate, propylene glycol, 1,3-butyl glycol oil, glycerol fatty ester, polyethylene glycol, or sorbitan fatty acid ester.

If the formulation of the present invention is suspension, it may contain, as carrier components, a liquid diluent, such as water, ethanol, or propylene glycol, and a suspending agent, such as ethoxylated isostearyl alcohol, polyoxyethylene sorbitol ester, polyoxyethylene sorbitan ester, and microcrystalline cellulose, aluminum metahydroxide, bentonite, agar, or tragacanth.

If the formulation of the present invention is a surfactant-containing cleansing, it may contain, as carrier components, aliphatic alcohol sulfate, aliphatic alcohol ether sulfate, sulfosuccinic monoester, isethionate, imidazolium derivatives, methyl taurate, sarcosinate, fatty acid amide ether sulfate, alkyl amido betaine, aliphatic alcohol, fatty acid glyceride, fatty acid diethanolamide, vegetable oil, lanoline derivatives, or ethoxylated glycerol fatty acid ester.

In the present invention, the term "containing as an active ingredient" means that an effective amount of ingredient is contained, which results in improvement, prevention, or treatment of allergic dermatitis and the amount may vary depending on severity of disease and a type of formulation, and the number of application may also vary depending on age, weight, and individual conditions of an applicable target. In the present invention, the term "allergic dermatitis" means all the diseases classified as allergic dermatitis in the art regardless of cause, either induced directly or indirectly. Typically, atopic dermatitis is classified into infancy atopic dermatitis, childhood atopic dermatitis, adult atopic dermatitis, and pregnancy atopic dermatitis, according to the time when the subject is affected by the disease. In the present invention, atopic dermatitis includes all types of atopic dermatitis described above.

In the present invention, an "allergic dermatitis" condition means a condition in which infection site is changed by allergic dermatitis, and such conditions both include a condition which is regarded as a skin disease and a condition which is not regarded as a skin disease.

In the present invention, the term "treatment" encompasses a complete cure of allergic dermatitis symptoms and partial cure, improvement or alleviation of allergic dermatitis symptoms after applying the pharmaceutical composition of the present invention to a site with allergic dermatitis.

In the present invention, the term "prevention" means activities which decrease emergence of allergic dermatitis symptoms by applying the pharmaceutical composition of the present invention to the skin in advance, and thus suppressing occurrence of allergic dermatitis symptoms on the skin in advance.

Further, in the present invention, the term "improvement" means amelioration, reduction, prevention, or disappearance of symptoms.

Furthermore, in the present invention, the term "active ingredient" means an ingredient showing an activity alone or an activity with a carrier which is not active.

The pharmaceutical composition of the present invention is administered in a pharmaceutically effective amount.

In the present invention, the term "pharmaceutically effective amount" means a sufficient amount to treat a disease at a reasonable benefit/risk ratio applicable to medical treatment and improvement. The effective amount can be determined depending on a race, kind, severity, age and sex of a subject, activity of medicine, sensitivity to medicine, administration time, administration route and excretion rate, treatment duration, factors including medicine(s) used at the same time and other factors commonly known in the medical field.

In the present invention, the term "subject" means all kinds of animals including humans already having or likely to have an allergic skin disease. When the composition which contains the GPCR19 agonist, specifically sodium taurodeoxycholate (HY2191) or its derivative(s) is administered to the subject according to the present invention, the disease can be effectively prevented or treated.

Hereinafter, examples will be described in order to describe the present invention in more detail. However, the examples according to the present invention can be modified in various ways, and the right scope of the present invention is not limited to the examples to be described below.

EXAMPLE

Example 1

Sample Preparation

For the first type of formulation, sodium taurodeoxycholate powder was dissolved so as to be 2.5% or 5% in a solvent (70% polyethylene glycol 400 and 30% ethanol in distilled water) and filtered with a 0.4 μm filter. To make second type of formulation, sodium taurodeoxycholate powder was dissolved so as to be 5% in a hyaluronic acid gel. The 5 g sodium taurodeoxycholic acid was mixed with 20 ml distilled water and was dissolved. The 80 mg chlorobutanol and 70 ml distilled water were mixed together with the 25% sodium taurodeoxycholic acid solution described above. One gram of hyalnuronic acid was added and mixed together with the solution. Distilled water was added to make up 100 ml.

Experimental Example 1

Animal Model of Atopic Dermatitis

In order to test efficacy of the sodium taurodeoxycholate (HY2191) composition on atopic dermatitis, dermatitis lesion was induced at the shaved-back of 6 weeks old male Balb/C mice. DNCB (2,4-dinitro-1-chlorobenzene, Sigma) was used as a hapten.

Five mice for each group were tested. The amount of IgE in blood of mice was measured to evaluate an inhibitory effect of a medication on IgE production. To make skin lesion of atopic dermatitis, 100 μL of a DNCB solution (2.5% in acetone) was applied on the shaved-back of the mouse at day 1. One hundred μL of DNCB (1% in acetone) was applied at day 4 and 100 μL of 0.2% DNCB in acetone at day 10.

From the day 7 to the day 14, 100 μL of the composition of 2.5% or 5% sodium taurodeoxycholate (HY2191) of example 1 was applied on the back of mice twice a day. Maxidex ointment (Dexamethasone, Alcon Korea) and Protopic ointment (Tacrolimus, Astellas Pharma Korea) were used for positive control groups and only a vehicle was used for a negative control group.

Experimental Example 2

Efficacy of Sodium Taurodeoxycholate on Atopic Dermatitis Evaluated by Gross Pathology and Clinical Scores Calculated Thereby In order to evaluate the efficacy of sodium taurodeoxycholate (HY2191) on atopic dermatitis, atopic dermatitis was induced on shaved-back of Balb/C mice with DNCB according to experimental example 1 and clinical scores of atopic dermatitis lesions incurred on the back of animal model was evaluated on day 15. To evaluate clinical scores at day 15, (1) the frequency of scratching for 2 minutes, (2) the severity of erythema/hemorrhage, (3) edema, (4) excoriation/erosion, and (5) scaling/dryness were graded and were scored from 0 (none) to 3 (severe), making the worst score 15 for the most severe subject. The every subject in every group was evaluated by three people in a double-blind method. The mean clinical score of individual mouse was calculated.

Figure 1B:
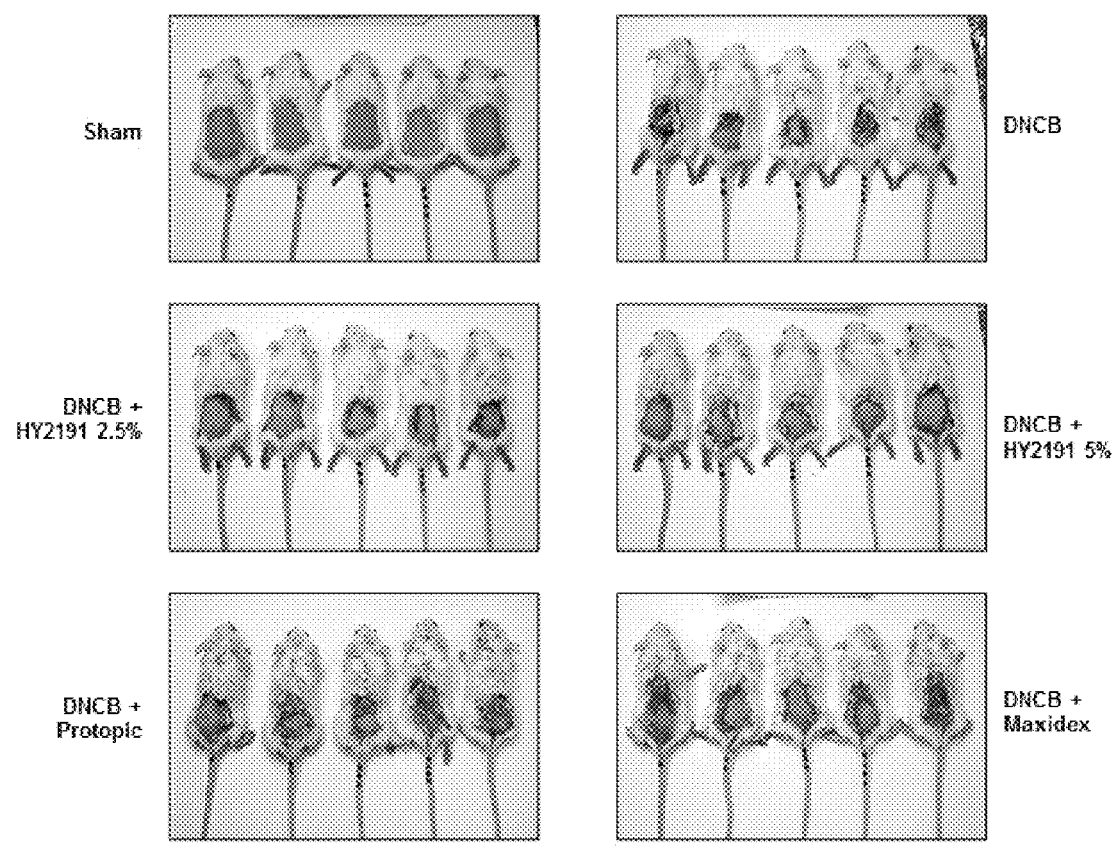
Figure 2:
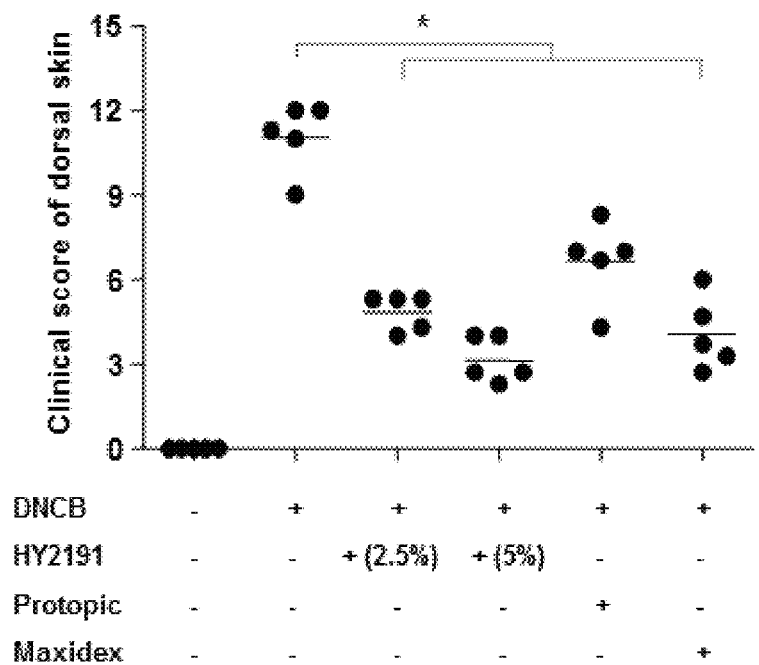
FIG. 2 shows clinical scores of dorsal skin.

Compared to the negative control group that was treated with vehicle only without sodium taurodeoxycholate (HY2191), the group treated with sodium taurodeoxycholate (HY2191) showed better clinical score (FIG. 1a, FIG. 1b and FIG. 2) significantly. Further, compared to the positive control group that received Maxidex ointment or Protopic ointment, the group of mice that received 5% sodium taurodeoxycholate (HY2191) showed better clinical scores (FIG. 1a, FIG. 1b and FIG. 2).

Experimental Example 3

Efficacy of Sodium Taurodeoxycholate on Atopic Dermatitis Evaluated by Measuring Serum Cytokines After the clinical evaluation described at Experimental Example 2, a mixture containing 0.4% of Zoletil (Virbac, Milano Italy) and 0.04% of Rompun (Bayer Korea) in normal saline was injected i.p. to anesthetize each mouse. Blood samples were collected from the heart of the mice. The serum was prepared to measure the concentration of IgE using enzyme immunoassay (Mouse IgE ELISA, BD). ELISA kits (eBioscience) were used to measure concentrations of TH1 cytokines (IFN-γ, IL-2) or TH2 cytokine (IL-4) in the serum.

Figure 3:
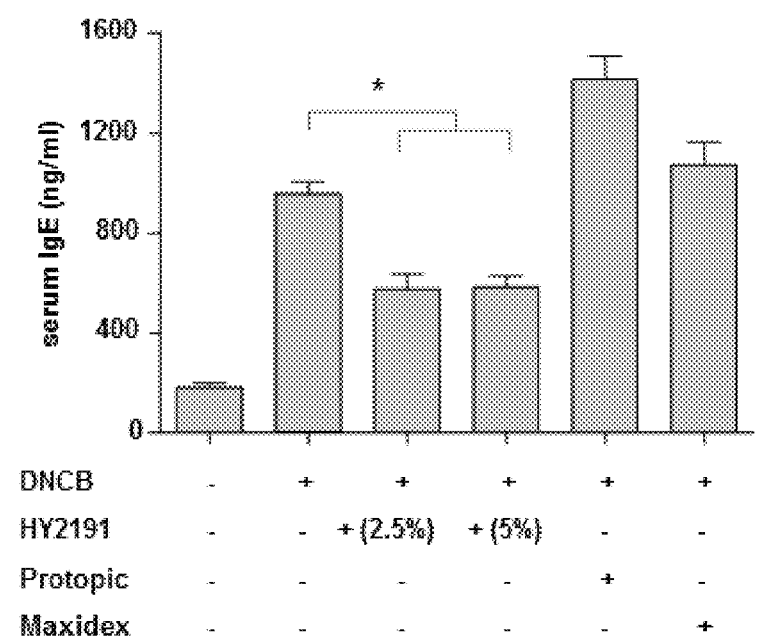
FIG. 3 shows serum IgE levels.

As shown in FIG. 3, the serum IgE levels were significantly lower in the group of mice treated with sodium taurodeoxycholate (HY2191), compared with the mice in positive control groups (groups of mice treated with Maxidex ointment or Protopic ointment). It clearly shows that 2.5% or 5% sodium taurodeoxycholate (HY2191) is effective in inhibiting serum IgE production, a pathognomonic feature of atopy (FIG. 3).

Figure 4:
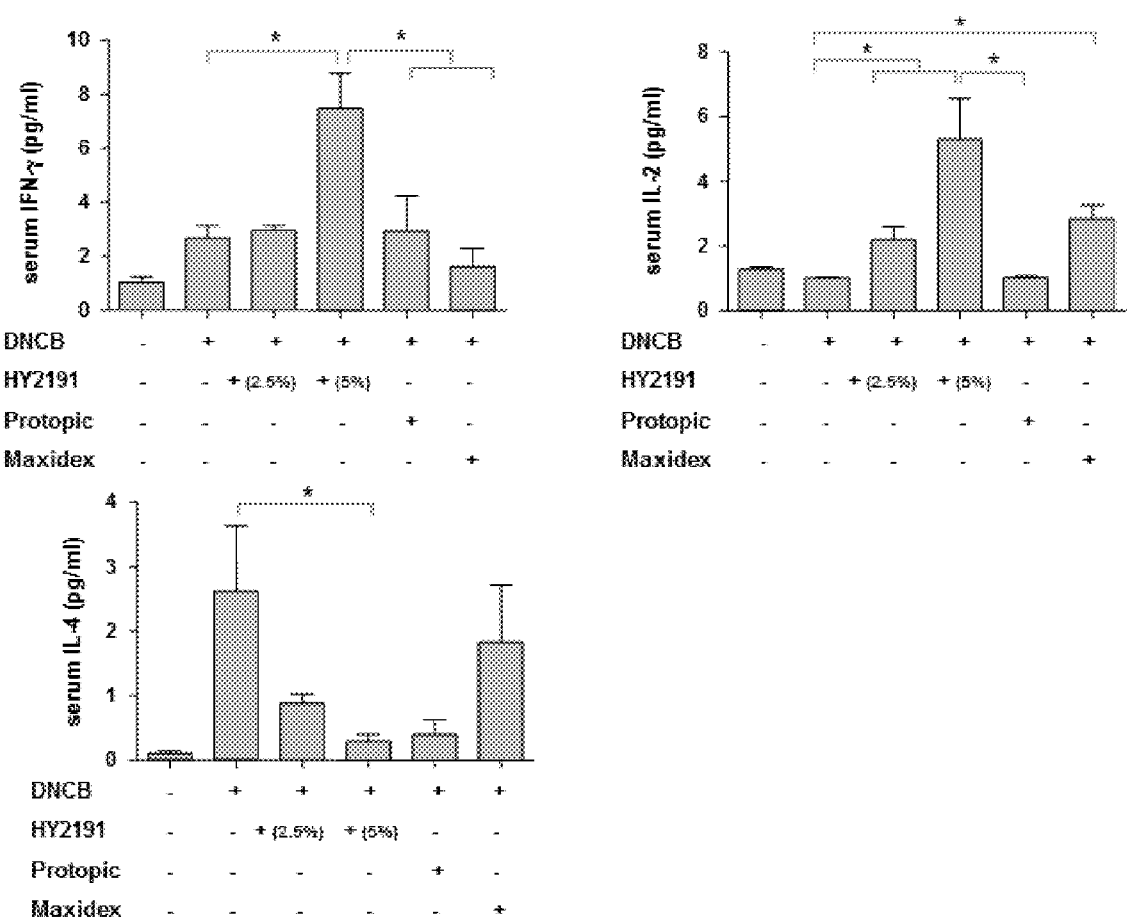
FIG. 4 shows TH1/TH2 cytokines (IL-4, IFN-γ and IL-2) levels of serum.

As shown in FIG. 4, the level of IFN-γ and IL-2 (TH1 cytokines) was increased significantly in the group of mice treated with 5% sodium taurodeoxycholate (HY2191) far better than control group of mice treated with Protopic or Maxidex (p<0.05). The level of IL-4 (TH2 cytokine) was decreased significantly in the group of mice treated with 5% sodium taurodeoxycholate (HY2191) better than control group of mice treated with Protopic or Maxidex (p<0.05).

Experimental Example 4

Efficacy of Sodium Taurodeoxycholate on Atopic Dermatitis Evaluated by Histopathology of Skin The dorsal skin flaps of the mice were fixed in a 10% formalin solution for 24 hours and then washed with distilled water. The paraffin blocks of the fixed skins were prepared and sectioned (thickness of 7 μm). They were stained with hematoxylin and eosin (H&E) (FIG. 5a). The thickness of epidermis and the dermis of mice treated with DNCB only were 320.2±21.6 μm and 930.2±34.2 μm, respectively. It was comparable with the thickness of the epidermis (26.1±1.0 μm) and the dermis (384.7±11.4 μm) of the mice in a sham group, which was not treated with DNCB (FIG. 5). Interestingly, the thickness of the epidermis from the group of atopic mice treated with 2.5% sodium taurodeoxycholate (HY2191), 5% sodium taurodeoxycholate (HY2191), Protopic, or Maxidex, were 105.3±7.0 μm, 75.0±8.4 μm, 123.1±14.8 μm, and 51.7±7.1 μm, respectively. It was comparable with thickness of epidermis from the group of mice treated with DNCB only (320.2±21.6 μm, p<0.05). The thickness of dermis from the group of atopic mice treated with 2.5% sodium taurodeoxycholate (HY2191), 5% sodium taurodeoxycholate (HY2191), or Protopic were 616.0±21.1 μm, 521.7±18.3 μm, and 572.6±20.2 μm, respectively. It was comparable with the thickness of dermis from the group of mice treated with DNCB only (930.2±34.2 μm, p<0.05). As was reported previously, the thickness of dermis from the group of mice treated with Maxidex (310.3±15.3 μm) was significantly thinner than that of dermis from the sham group of mice which was not treated with DNCB (384.7±11.4 μm, p<0.05).

Figure 6A:
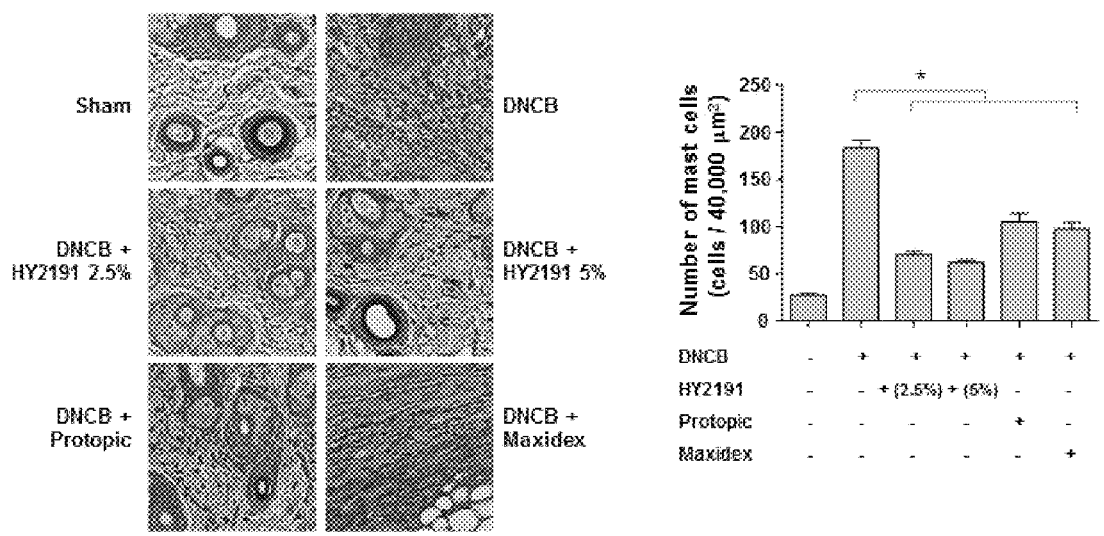
FIGS. 6a to 6c show infiltration of a mast cell (A) revealed by staining with toluidine blue, eosinophil (B) stained with congo red, and neutrophil (C) stained with specific esterase (naphthol AS-D chloroacetate).
Figure 6B:
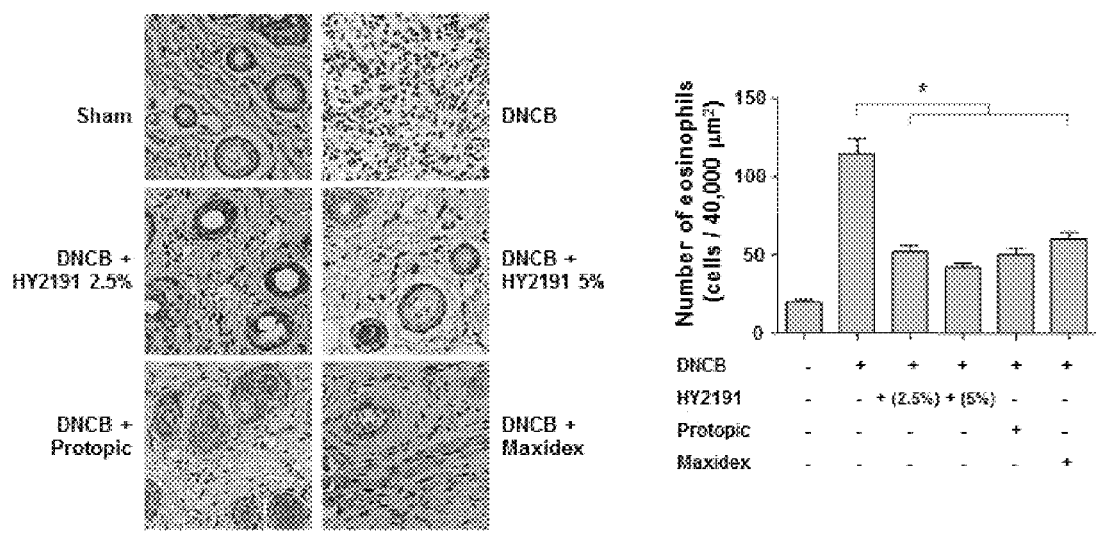
Figure 6C:
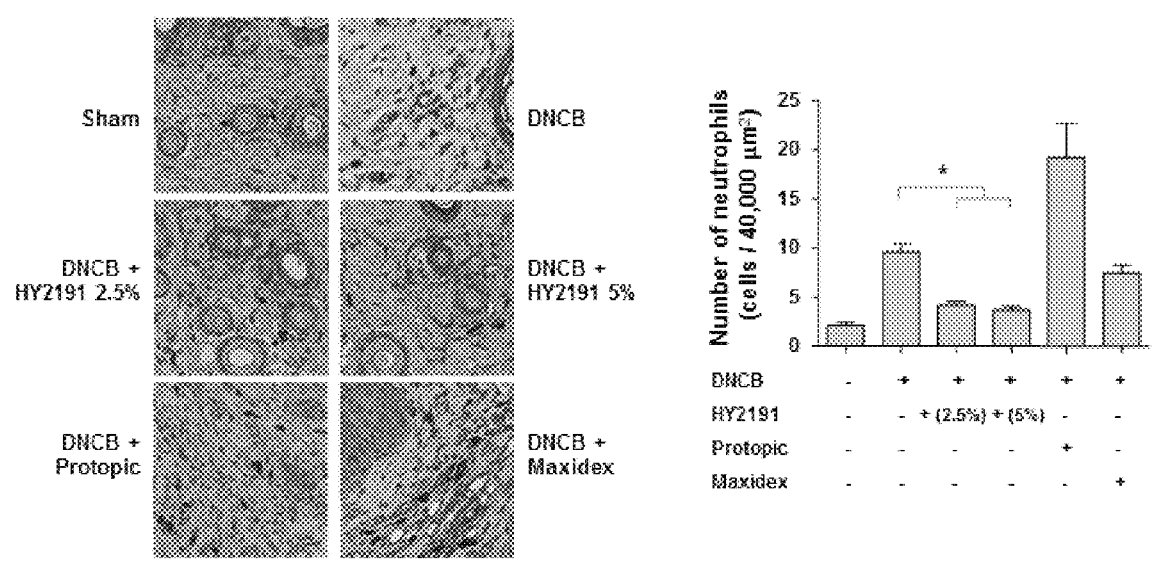

The number of mast cells, eosinophils, and neutrophils infiltrated into the dermis were counted after staining skins with toluidine blue, congo red, or specific esterase (Naphthol AS-D chloroacetate), respectively. The number of mast cells, eosinophils, and neutrophils in the dermis of mice treated with DNCB only were significantly higher than that of mice in a sham group (FIGS. 6a, 6b, and 6c). After treatment with sodium taurodeoxycholate (HY2191), the number of mast cells, eosinophils, and neutrophils in the skin of atopic mice were significantly decreased compared with that of mice in a vehicle-treated group (p<0.05). On the other hand, the number of neutrophils critical for acute inflammation was increased in the group of atopic mice treated with Protopic. The group of mice treated with Maxidex did not show significant decrease in number of neutrophils compared to group of atopic mice treated with vehicle.

Hereinafter, the respective manufacturing examples according to the present invention will be described. The following manufacturing examples are provided only for better understanding of the present invention, but the methods for manufacturing the formulations according to the present invention are not limited to the following manufacturing examples.

Manufacturing Example

Manufacturing Process of Powder Formulation

| | |
|---|---|
| Sodium taurodeoxycholate(HY2191) | 10 mg |
| Sucrose | 100 mg |
| Talc | 10 mg |

The above-described components are prepared in powder form and then mixed and filled into an air-tight bag so as to prepare a powder formulation.

Manufacturing Example 2

Manufacturing Process of Tablet Formulation

| | |
|---|---|
| Sodium taurodeoxycholate(HY2191) | 10 mg |
| Starch | 100 mg |
| Sucrose | 100 mg |
| Magnesium Stearate | 2 mg |

The above-described ingredients are blended according to a conventional method of manufacturing a tablet and then compressed into a tablet.

Manufacturing Example 3

Manufacturing Process of Capsule Formulation

| | |
|---|---|
| Sodium taurodeoxycholate(HY2191) | 10 mg |
| Crystalline cellulose | 3 mg |
| Lactose | 15 mg |
| Magnesium Stearate | 1 mg |

The above-described ingredients are mixed according to a conventional method of manufacturing a capsule and then filled into a gelatin capsule to make a capsule.

Manufacturing Example 4

Manufacturing Process of Granule Formulation

| | |
|---|---|
| Sodium taurodeoxycholate(HY2191) | 10 mg |
| Soybean extract | 50 mg |
| Glucose | 200 mg |
| Starch | 500 mg |

The above-described components are mixed and added with 100 mL of 30% ethanol and then dried at 60° C. so as to form granules, and the granules are filled into a bag so as to form a granulation.

Manufacturing Example 5

Manufacturing Process of Pill Formulation

| | |
|---|---|
| Sodium taurodeoxycholate(HY2191) | 10 mg |
| Lactose | 1,500 mg |
| Glycerin | 1,500 mg |
| Starch | 980 mg |

The above-described ingredients are mixed and then each pill is made weighing 4 g according to a conventional method of the pill manufacturing process.

Manufacturing Example 6

Manufacturing Process of Injection Formulation

| | |
|---|---|
| Sodium taurodeoxycholate(HY2191) | 10 mg |
| Mannitol | 180 mg |
| Sterile distilled water for injection | 2,970 mg |
| $Na_2HPO_4 \cdot 12H_2O$ | 30 mg |

The above-described ingredients are mixed and then manufactured so as to obtain each ampoule containing 2 mL according to a conventional method of the injection manufacturing process.

Manufacturing Example 7

Manufacturing Process of Liquid Formulation

| | |
|---|---|
| Sodium taurodeoxycholate(HY2191) | 10 mg |
| Isomerized glucose syrup | 10,000 mg |
| Mannitol | 5,000 mg |
| Purified water | Suitable amount |

The above-described ingredients are dissolved in purified water according to a conventional method of manufacturing liquid formulation, and added with a suitable flavoring, and then filled into a bottle to be sterilized, thereby creating a liquid formulation.

Manufacturing Example 8

Manufacturing Process of Soap

After 175 g of NaOH is blended with 330 mL of water and completely dissolved, 10 mg of sodium taurodeoxycholate is added little by little for about 30 minutes and mixed. The mixture is kept in a shady and airy place until dried.

Manufacturing Example 9

Manufacturing Process of Bath Products

After 10 mg of sodium taurodeoxycholate (HY2191) is heated around 60° C., sea salt is added to make a saturated solution and then water is evaporated. The solution was cooled at room temperature and then lyophilized after rapidly frozen. The lyophilized solid formulation is powdered to create a bath product.

Manufacturing Example 10

Manufacturing Process of Cleansing Lotion

TABLE 1

| | |
|---|---|
| Sodium taurodeoxycholate(HY2191) | 0.001 v/v % |
| Ethylenediaminetetraacetate | 0.02 |
| Methyl p-Hydroxybenzoate | 0.2 |
| Glycerin | 4 |
| Sodium hyaluronic acid | 2 |
| Propylene glycol | 3 |
| Carbomer | 5 |
| Cetearyl alcohol | 0.7 |
| Glyceryl stearate | 0.5 |
| Shea butter | 1 |
| Propyl p-Hydroxybenzoate | 0.1 |
| Macadamia nut oil | 1 |
| Sesquioleate | 0.5 |
| Glyceryl stearate | 1 |
| Polyoxyethylene sorbitan monooleate | 2 |
| Polydecene | 5 |
| Mineral oil | 20 |
| Dimethicone | 5 |
| Stearyl dimethicone | 2 |
| Triethanolamine | 0.05 |
| Flavor | Suitable amount |
| Pigment | Suitable amount |
| Purified water | The amount of remains |

A cleansing lotion is created, using the ingredients described above, according to a conventional method of manufacturing a cleansing lotion in the cosmetic manufacturing industry.

Manufacturing Example 11

Manufacturing Process of Skin Lotion/Softener/Toner

TABLE 2

| | |
|---|---|
| Sodium taurodeoxycholate(HY2191) | 0.001 v/v % |
| Methyl ρ-Hydroxybenzoate | 0.2 |
| Ethylenediaminetetraacetate | 0.02 |
| 1,3-Butylene glycol | 0.02 |
| Allantoin | 3 |
| Sodium hyaluronic acid | 5 |
| Carbomer | 0.1 |
| Cetostearyl alcohol | 0.7 |
| Propyl ρ-Hydroxybenzoate | 0.1 |
| Sorbitan olivate | 1.5 |
| Soy lecithin | 0.2 |
| Dimethicone | 0.2 |
| Cetyl octanoate | 0.2 |
| Shea butter | 0.2 |
| Sodium polyacrylate | 3 |
| Triethanolamine | 0.1 |
| Imidazolidinyl urea | 0.3 |
| Flavor | Suitable amount |
| Pigment | Suitable amount |
| Purified water | The amount of remains |

A skin lotion/softener/toner is created, using the ingredients described above, according to a conventional method of manufacturing a skin lotion/softener/toner in the cosmetic manufacturing industry.

Manufacturing Example 12

Manufacturing Process of Serum

TABLE 3

| | |
|---|---|
| Sodium taurodeoxycholate(HY2191) | 0.001 v/v % |
| Jojoba | 5 |
| Black sesame | 2 |
| Sweet almond | 3 |
| Emulsifying wax | 1 |
| Vitamin E | 1 |
| Glycerin | 2 |
| Hyaluronic acid | 1 |
| Marine elastin | 1 |
| Purified water | The amount of remains |

A serum is created, using the ingredients described above, according to a conventional method of manufacturing a serum in the cosmetic manufacturing industry.

Manufacturing Example 13

Manufacturing Process of Lotion

TABLE 4

| | |
|---|---|
| Sodium taurodeoxycholate(HY2191) | 0.001 v/v % |
| Methyl ρ-Hydroxybenzoate | 0.2 |
| Ethylenediaminetetraacetate | 0.02 |
| 1,3-Butylene glycol | 0.02 |
| Allantoin | 3 |
| Sodium hyaluronic acid | 5 |
| Carbomer | 0.1 |
| Cetostearyl alcohol | 0.7 |
| Propyl ρ-Hydroxybenzoate | 0.1 |
| Sorbitan olivate | 1.5 |
| Soy lecithin | 0.2 |
| Dimethicone | 0.2 |
| Cetyl octanoate | 0.2 |
| Shea butter | 0.2 |
| Sodium polyacrylate | 3 |
| Triethanolamine | 0.1 |
| Imidazolidinyl urea | 0.3 |
| Flavor | Suitable amount |
| Pigment | Suitable amount |
| Purified water | The amount of remains |

A lotion is created, using the ingredients described above, according to a conventional method of manufacturing a lotion in the cosmetic manufacturing industry.

Manufacturing Example 14

Manufacturing Process of Essence

TABLE 5

| | |
|---|---|
| Sodium taurodeoxycholate(HY2191) | 0.001 v/v % |
| Allantoin | 0.05 |
| Ethylenediaminetetraacetate | 0.02 |
| Triethanolamine | 0.2 |
| Sodium hyaluronic acid | 7 |
| Imidazolidinyl urea | 0.15 |
| Sodium polyacrylate | 0.4 |
| Carbomer | 0.2 |
| Ethanol | 3 |
| Polyoxyetylene sorbitan monostearate | 0.2 |
| Methyl ρ-Hydroxybenzoate | 0.2 |
| Flavor | Suitable amount |
| Pigment | Suitable amount |
| Purified water | The amount of remains |

An essence is created, using the ingredients described above, according to a conventional method of manufacturing an essence in the cosmetic manufacturing industry.

Manufacturing Example 15

Manufacturing Process of Cream

TABLE 6

| | |
|---|---|
| Sodium taurodeoxycholate(HY2191) | 0.001 v/v % |
| Ethylenediaminetetraacetate | 0.02 |
| Allantoin | 0.1 |
| Glycerin | 5 |
| Methyl ρ-Hydroxybenzoate | 0.2 |
| Sodium hyaluronic acid | 6 |
| Carbomer | 0.1 |
| Cetostearyl alcohol | 1.7 |
| Polydecene | 2 |
| Squalane | 2 |
| Propyl ρ-Hydroxybenzoate | 0.1 |
| Butylene glycol dicaprylate | 3 |
| Cetyl octanoate | 5 |
| Microcrystalline lead | 0.1 |
| Triethyl pentanediol | 0.1 |
| Shea butter | 0.2 |
| Sorbitan olivate | 0.3 |
| Cyclomethicone | 0.3 |
| Stearyl dimethicone | 0.5 |
| Imidazolidinyl urea | 0.15 |
| Flavor | Suitable amount |
| Pigment | Suitable amount |
| Purified water | Suitable amount |

A cream was created, using the ingredients described above, according to a conventional method of manufacturing a cream in the cosmetic manufacturing industry.

Manufacturing Example 16

Manufacturing Process of Pack

TABLE 7

| | |
|---|---|
| Sodium taurodeoxycholate(HY2191) | 0.001 v/v % |
| Ethylenediaminetetraacetate | 0.02 |
| Betaine | 3 |
| Glyceryl polymethacrylate | 2 |
| Allantoin | 0.1 |
| Sodium hyaluronic acid | 2 |
| Glycerin | 3 |
| Dipropylene glycol | 5 |
| Methyl p-Hydroxybenzoate | 0.2 |
| Polyvinyl alcohol | 10 |
| Polyoxyetylene sorbitan monooleate | 0.9 |
| Sesquioleate | 0.3 |
| Jojoba ester | 2 |
| Cetearyl alcohol | 1.5 |
| Petrolatum | 0.5 |
| Flavor | Suitable amount |
| Pigment | Suitable amount |
| Purified water | Suitable amount |

A pack is created, using the ingredients described above, according to a conventional method of manufacturing a pack in the cosmetic manufacturing industry.

Manufacturing Sample 17

Manufacturing Process of Massage Cream

TABLE 8

| | |
|---|---|
| Sodium taurodeoxycholate(HY2191) | 0.001 v/v % |
| Purified water | Suitable amount |
| Glycerin | 4.0 |
| Vaseline | 3.5 |
| Triethanolamine | 0.5 |
| Liquid Paraffin | 24.5 |
| Squalane | 2.5 |
| Beeswax | 2.1 |
| Tocopheryl Acetate | 0.1 |
| Carbopol | 1.0 |
| Sorbitan Sesquioleate | 3.1 |
| Flavor | Small amount |
| Preservative | Small amount |

A massage cream is created, using the ingredients described above, according to a conventional method of manufacturing a massage cream in the cosmetic manufacturing industry.

Manufacturing Example 18

Manufacturing Process of Makeup Base

TABLE 9

| | |
|---|---|
| Sodium taurodeoxycholate(HY2191) | 0.001 v/v % |
| Purified water | Suitable amount |
| Coated Silica | 1 |
| Silica | 10 |

TABLE 9-continued

| | |
|---|---|
| Titanium Dioxide | 5 |
| Zinc Oxide | 3 |
| Pigment | 1 |
| Plate powder | The amount of remains |

A makeup base is created, using the ingredients described above, according to a conventional method of manufacturing a makeup base in the cosmetic manufacturing industry.

Manufacturing Example 19

Preparation of Powder Pact

TABLE 10

| | |
|---|---|
| Sodium taurodeoxycholate(HY2191) | 0.001 v/v % |
| Purified water | Suitable amount |
| Mica | 15 |
| Titanium Dioxide | 7 |
| Silicon Oil | 3 |
| Ester-based Oil | 3 |
| Pigment | Suitable amount |
| Flavor | Suitable amount |
| Talc | The amount of remains |

A powder pact is created, using the ingredients described above, according to a conventional method of manufacturing a powder pact in the cosmetic manufacturing industry.

Manufacturing Example 20

Manufacturing Process of Two-Way Cake

TABLE 11

| | |
|---|---|
| Sodium taurodeoxycholate(HY2191) | 0.001 v/v % |
| Purified water | Suitable amount |
| Mica | 15 |
| Titanium Dioxide | 12 |
| Silicon Oil | 3 |
| Ester-based oil | 5 |
| Pigment | Suitable amount |
| Flavor | Suitable amount |
| Talc | The amount of remains |

A two-way cake was prepared using the ingredients described above, according to a conventional method of preparing a two-way cake in the cosmetic manufacturing industry.

INDUSTRIAL APPLICABILITY

The prevalence of allergic skin diseases has been gradually increasing. Currently, anti-histamines or steroids have been used to relieve symptoms, but there are few medicines that can cure atopic skin diseases. This invention suggests that the pharmaceutical composition containing a GPCR19 agonist, specifically, sodium taurodeoxycholate (HY2191) and/or its derivatives, are highly effective for treating atopic dermatitis. The composition containing a GPCR19 agonist, specifically, sodium taurodeoxycholate (HY2191) and/or its derivatives might be used for an external preparation or a cosmetic composition for preventing and improving allergic skin diseases.

The invention claimed is:

1. A method of treating allergic skin diseases comprising administering an effective amount of a composition to a subject in need of such treatment, wherein:
the composition's active ingredient consists of sodium taurodeoxycholate; and
the sodium taurodeoxycholate is formulated in the form of an external preparation.

2. The method of treating allergic skin diseases according to claim 1, wherein the sodium taurodeoxycholate reduces the levels of serum IgE and serum TH2 cytokine and increases the level of serum TH1 cytokine.

3. The method of treating allergic skin diseases according to claim 1, wherein the external preparation is formulated as any of the form selected from the group consisting of cream, gel, ointment, emulsion, suspension, spray and a transdermal patch.

4. The method of treating allergic skin diseases according to claim 1, wherein the sodium taurodeoxycholate is applied with the amount of 0.01 to 1000 mg per day.

5. The method of treating allergic skin diseases according to claim 1, wherein the allergic skin diseases are selected from the group consisting of allergic dermatitis, atopic dermatitis, contact dermatitis, hives, and pruritus.

6. A method for cosmetic care to soothe or alleviate allergic skin diseases comprising topically applying onto any body skin area of a subject in need of such care a cosmetically effective amount of a composition, wherein the composition's active ingredient consists of sodium taurodeoxycholate.

7. The method for cosmetic care to sooth or alleviate allergic skin diseases according to claim 6, wherein the sodium taurodeoxycholate is prepared in any one or more formulations selected from the group consisting of soap, cleansing foam, cleansing cream, cleansing water, a bath product, skin lotion, skin softener, skin toner, lotion, cream, essence, astringent, emulsion, gel, lipstick, spray, shampoo, conditioner, treatment, body cleanser, pack, massage cream, face powder, compact, foundation, two-way cake, and makeup base for allergic skin diseases.

8. The method for cosmetic care to sooth or alleviate allergic skin diseases according to claim 6, wherein the allergic skin diseases are selected from the group consisting of allergic dermatitis, atopic dermatitis, contact dermatitis, hives, and pruritus.

* * * * *